(12) United States Patent
Ur

(10) Patent No.: US 9,349,301 B2
(45) Date of Patent: May 24, 2016

(54) SENSOR-BASED MOVEMENT GUIDANCE

(75) Inventor: Shmuel Ur, Shorashim (IL)

(73) Assignee: Empire Technology Development LLC, Wilmington, DE (US)

( * ) Notice: Subject to any disclaimer, the term of this patent is extended or adjusted under 35 U.S.C. 154(b) by 100 days.

(21) Appl. No.: 13/129,745

(22) PCT Filed: Jan. 28, 2011

(86) PCT No.: PCT/US2011/022912
§ 371 (c)(1),
(2), (4) Date: May 17, 2011

(87) PCT Pub. No.: WO2012/102730
PCT Pub. Date: Aug. 2, 2012

(65) Prior Publication Data
US 2013/0293344 A1 Nov. 7, 2013

(51) Int. Cl.
*G09B 21/00* (2006.01)
*G08B 23/00* (2006.01)
(Continued)

(52) U.S. Cl.
CPC ............ *G09B 21/001* (2013.01); *A61B 5/1112* (2013.01); *A61H 3/061* (2013.01);
(Continued)

(58) Field of Classification Search
CPC ........... A61B 2218/00; A61B 2562/00; A61B 2562/06; A61B 2560/0266; A61B 5/68; A61B 5/6807; A61B 5/684; A61B 5/6843; A61B 5/6887; A61B 5/1036; A61B 2562/0247; A61B 2562/04; A61B 5/1116; A61B 5/112; A61B 5/1118; A61B 5/1124; A61B 5/6828; A61B 5/6829; A61B 5/1117; A61B 5/0048; A61H 1/008; A61H 2230/80; A61H 2230/62; A61H 2205/125; A61H 2201/1657; A43B 1/00; A43B 5/00; A43B 9/00; A43B 13/00; G01G 21/00; G01G 23/00; G01G 9/00; G01C 22/00; G01C 22/006; G01C 19/58; G01C 21/3626; G01C 21/3644; G01C 21/3652; G01C 21/3641; G01C 21/34; G01C 21/20
USPC .......... 340/4.1, 995.1, 539.11, 539.13, 407.1, 340/573.7, 944, 537.7, 665; 701/200, 201, 701/205, 209, 300, 302, 208, 213, 217, 466, 701/469, 494; 382/123, 232, 248, 250; 455/415, 557; 482/79, 95, 98; 73/65.01
See application file for complete search history.

(56) References Cited

U.S. PATENT DOCUMENTS 5,807,111 A   9/1998  Schrader
6,066,075 A * 5/2000  Poulton ............................. 482/8
(Continued)

FOREIGN PATENT DOCUMENTS

GB       2460278 A      11/2009

OTHER PUBLICATIONS

W. Heuten, et al., "Tactile Wayfinder: A Non-Visual Support System for Wayfinding", Proceedings: NordiCHI 2008, Oct. 20-22, 2008, pp. 172-181.
(Continued)

*Primary Examiner* — Mirza Alam
(74) *Attorney, Agent, or Firm* — Brundidge & Stanger, P.C.

(57) ABSTRACT

Technologies are generally described for methods, instructions, and applications for a user-guidance system. In some examples, the system may include sensors to measure current weight distribution of a user of the user-guidance system and to transmit resulting measured weight distribution data, a guidance apparatus to calculate a subsequent user movement based on at least the measured weight distribution data and to transmit resulting user movement instructions, and an actuator to produce actuating signals, based on at least the user movement instructions, that provide instructions for the subsequent user movement.

34 Claims, 5 Drawing Sheets

(51) Int. Cl.
G08G 1/095 (2006.01)
A63B 23/08 (2006.01)
A61H 3/06 (2006.01)
A61B 5/11 (2006.01)
G01S 15/93 (2006.01)
A61B 5/00 (2006.01)
A61B 5/103 (2006.01)

(52) U.S. Cl.
CPC .............. *G01S 15/93* (2013.01); *A61B 5/0022* (2013.01); *A61B 5/1038* (2013.01); *A61B 5/1126* (2013.01); *A61B 5/6828* (2013.01); *A61B 5/6829* (2013.01); *A61B 2560/0242* (2013.01); *A61B 2562/0252* (2013.01); *A61H 2201/5007* (2013.01); *A61H 2201/5012* (2013.01); *A61H 2201/5061* (2013.01); *A61H 2201/5092* (2013.01); *A61H 2201/5097* (2013.01)

(56) References Cited

U.S. PATENT DOCUMENTS

| | | | |
|---|---|---|---|
| 6,275,213 | B1 | 8/2001 | Tremblay et al. |
| 6,285,379 | B1 | 9/2001 | Gallery |
| 6,320,496 | B1 | 11/2001 | Sokoler et al. |
| 6,353,773 | B1 | 3/2002 | Takenaka |
| 6,671,618 | B2* | 12/2003 | Hoisko ..................... 701/466 |
| 6,864,877 | B2 | 3/2005 | Braun et al. |
| 7,788,032 | B2 | 8/2010 | Moloney |
| 7,839,269 | B2 | 11/2010 | Steger et al. |
| 7,864,991 | B2 | 1/2011 | Espenlaub et al. |
| 2006/0286972 | A1* | 12/2006 | Kates ........................... 455/415 |
| 2007/0016425 | A1 | 1/2007 | Ward |
| 2007/0073196 | A1* | 3/2007 | Tanaka et al. ................ 600/595 |
| 2007/0129907 | A1* | 6/2007 | Demon ....................... 702/127 |
| 2007/0213930 | A1 | 9/2007 | Sakamoto et al. |
| 2007/0260418 | A1* | 11/2007 | Ladetto et al. ............... 702/150 |
| 2008/0120029 | A1* | 5/2008 | Zelek et al. ................... 701/213 |
| 2009/0062092 | A1 | 3/2009 | Mortimer et al. |
| 2009/0088659 | A1 | 4/2009 | Graham et al. |
| 2009/0260426 | A1* | 10/2009 | Lieberman et al. .......... 73/65.01 |
| 2010/0004860 | A1 | 1/2010 | Chernoguz et al. |
| 2010/0117837 | A1 | 5/2010 | Stirling et al. |
| 2011/0009241 | A1 | 1/2011 | Lane et al. |

OTHER PUBLICATIONS

Robert W. Lindeman, "The Design and Deployment of a Wearable Vibrotactile Feedback System", Proc. of the 8$^{th}$ IEEE Int'l Symp. on Wearable Computers, Oct. 31-Nov. 3, 2004, Arlington, VA, USA, pp. 56-59.
"Navigation and Information System for Visually Impaired People" by Kopeček, et al., May 1997.
"Haptic Navigation in Mobile Context" by H. Venesvirta., Dec. 2008, pp. 1-16.
International Search Report for PCT/US2011/022912 mailed Apr. 12, 2011.
International Search Report and Written Opinion for PCT International Application No. PCT/US2011/051913 mailed Feb. 13, 2012.
"Is There in Truth No Beauty?",Wikipedia, http://en.wikipedia.org/wiki/Is_There_in_Truth_No_Beauty%3F, Jun. 6, 2011, pp. 1-3.
"A Wearable Haptic Navigation Guidance System" by S. Erthan, et al., Oct. 1998, pp. 164-165.
"AJ the Blind Tango Dancer," accessed at http://www.youtube.com/watch?v=94NoViVkKx4, accessed on Dec. 30, 2014, pp. 1-2.
"Blind bike trials video," accessed at http://www.youtube.com/watch?v=9f7FlQhDihM, accessed on Dec. 30, 2014, pp. 1-2.
"Blind Rider," accessed at http://www.youtube.com/watch?v=B4xUijM1jpU, accessed on Dec. 30, 2014, pp. 1-2.

"Computer-Based Navigation System for Blind People," accessed at https://web.archive.org/web/20090917075013/http://www.axistive.com/computer-based-navigation-system-for-blind-people.html, Published on Jun. 27, 2007, pp. 1-3.
"da Blind Surfer of Kaua'l," accessed at http://www.youtube com/watch?v=eZj5qEDeaT8, accessed on Dec. 30, 2014, pp. 1-2.
"Facing the Waves," accessed at http://www.youtube.com/watch?v=5sIRTg3allQ , accessed on Dec. 30, 2014, pp. 1-2.
"Lead and follow," accessed at https://web.archive.org/web/20110608191633/http://en.wikipedia.org/wiki/Lead_and_follow, last modified on Apr. 26, 2011, pp. 1-4.
"Motion capture," accessed at https://web.archive.org/web/20100715231753/http://www.search.com/reference/Motion_capture, accessed on Dec. 23, 2014, pp. 1-9.
"RG, Robotic guide for the blind, Guides a visually impaired individual," accessed at http://www.youtube.com/watch?v=TMvio63yoJs, accessed at Dec. 30, 2014, pp. 1-2.
"Sports and Activity Rules for those with Visual Impairments," accessed at https://web.archive.org/web/20110209121154/http://www.recreationtherapy.com/tx/txblind.htm, accessed on Dec. 24, 2014, pp. 1-6.
"Wearable Interface using sensory illusion and distortion," accessed at https://web.archive.org/web/20100221070630/http://www.brl.ntt.co.jp/people/t-amemiya/research.html, accessed on Dec. 24, 2014, pp. 1-11.
"Weight transfer (dance move)," accessed at http://en.wikipedia.org/wiki/Weight_transfer_%28dance_move%29, last modified on Jul. 3, 2012, p. 1.
Amemiya, T., and Sugiyama, H., "Navigation in eight cardinal directions with pseudo-attraction force for the visually impaired," Systems, Man and Cybernetics, 2009. SMC 2009. IEEE International Conference on, pp. 27-32 (Oct. 11-14, 2009).
Cosetta., "Vibrating Body-Piercing Jewelry: Great Idea?," accessed at https://web.archive.org/web/20100430032747/http://inventorspot.com/articles/vibrating_bodypiercing_jewelry_great_idea_21197, accessed on Dec. 24, 2014, pp. 1-4.
Eaton, K., "Kinect Hacked to Control Humanoid Robot: First Steps to Avatar," accessed at https://web.archive.org/web/20110906004327/http://www.fastcompany.com/1713032/kinect-hacked-to-control-humanoid-robot-first-steps-to-avatar, Dated Dec. 29, 2010, pp. 1-2.
Ford, J., "Robot could guide humans through areas of low visibility," accessed at http://www.theengineer.co.uk/sectors/electronics/news/robot-could-guide-humans-through-areas-of-lowvisibility/1008224.article, Dated Apr. 6, 2011, pp. 1-2.
Iselin, T., "Blind Skier's Edge Adaptive Ski Clinincs With Blind Adventurer Erik Weihenmayer," accessed at https://web.archive.org/web/20110910200205/http://www.blindskiersedge.org/, accessed on Dec. 23, 2014, p. 1.
MacDonald, K., "Enjoying the Ride Without Seeing Where You're Going," accessed at https://web.archive.org/web/20110711062231/http://cityroom.blogs.nytimes.com/2010/10/22/enjoying-the-ride-without-seeing-where-youre-going/, posted on Oct. 22, 2010, pp. 1-12.
neilC, "Kinect Motion Control of Virtual World Avatars," accessed at http://web.archive.org/web/20110812152607/http://blog.knowsense.co.uk/blog_archives/2011/1/20/4731040.html, posted on Jan. 20, 2011, pp. 1-2.
Sandhana, L.,"GPS to Help the Blind Navigate," accessed at https://web.archive.org/web/20110831094920/http://www.wired.com/medtech/health/news/2003/06/59174, Dated Jun. 14, 2003, pp. 1-2.
Springer, S., "Chasing glory they can feel, not see," acceessed at http://www.boston.com/sports/specials/marathon/articles/2008/04/20/chasing_glory_they_can_feel_not_see/, Dated Apr. 20, 2008, pp. 1-2.
Trafton, A., "Feeling the way" accessed at https://web.archive.org/web/20100330094541/http://web.mit.edu/newsoffice/2009/touch-map.html, Dated Nov. 23, 2009, pp. 1-3.
Wieser, M., et al., "A Navigation Concept for Visually Impaired Pedestrians in an Urban Environment," Vermessung & Geoinformation, pp. 159-165 (Feb. 2007).
Zillner, S., et al., "The Right Move"—A Concept for a Video-Based Choreography Tool, Conference on Photogrammatic Computer Vision, pp. 1-4 (Aug. 2002).

* cited by examiner

SENSOR-BASED MOVEMENT GUIDANCE

CROSS-REFERENCE TO RELATED APPLICATION

This Application is the National Stage filing under 35 U.S.C. §371 of PCT Application Ser. No. PCT/US11/22912 filed on Jan. 28, 2011. The disclosure of the PCT Application is hereby incorporated herein by reference in its entirety.

TECHNICAL FIELD

The implementations and embodiments described herein pertain generally to providing guidance for the visually impaired, i.e., those individuals who are blind or with significantly diminished visual capabilities.

BACKGROUND

Guidance options for visually impaired people either involve significant reliance upon others, including other people or even animals, or restrict the pace and scope of the individual's movements.

For instance, a visually-impaired person using a cane relies upon other people in his/her immediate vicinity to be cognizant and cooperative lest the cane inadvertently becomes an obstruction, i.e., physical hazard, to those other people who may trip over or otherwise be impeded by the cane or even the visually-impaired person. Further, and particular to the visually-impaired person, the utility of the cane is limited to providing only step-by-step guidance with regard to obstacles in the immediate vicinity of the visually-impaired person; and, inanimate objects are incapable of effecting the aforementioned cognizance and cooperation towards the visually-impaired person, thus proving to be a potential obstruction to the person using the cane. Consequently, the movements of the visually-impaired person using the cane are restricted in terms of pace and physical scope.

A visually-impaired person relying upon a guide-dog is less reliant upon the cognizance and cooperation of other people in the vicinity of the visually-impaired person, relative to the person using a cane. However, the guide-dog-user is reliant upon, and therefore somewhat limited by, the guide-dog's training and subsequent guidance in familiar settings. Still, similar to the person using the cane, the person led by a guide-dog may be provided step-by-step guidance with regard to obstacles in his/her immediate vicinity, but a guide-dog is incapable of providing feedback regarding the landscape; and, thus, the pace and even the scope of the movements for the person led by a guide-dog are cautiously limited.

SUMMARY

In one example, a user-guidance system is generally described. In some embodiments thereof, the system may include sensors to measure current weight distribution of a user of the user-guidance system and to transmit resulting measured weight distribution data, a guidance apparatus to calculate a subsequent user movement based on at least the measured weight distribution data and to transmit resulting user movement instructions, and an actuator to produce actuating signals, based on at least the user movement instructions, that provide instructions for the subsequent user movement.

In another example, a guidance system may include at least one weight sensor to determine a user's current weight distribution, a user-adorned visual sensor to provide visual data regarding the user's physical surroundings, a guiding device to translate the user's movements in response to the user's current weight distribution and the visual data from the sensor into instructions to direct the user's physical movements, and at least one user-adorned actuator to translate the instructions from the guiding device into at least one appropriate physical stimulus to direct the user's movements.

In yet another example, a computer-readable medium for a user guidance system is generally described. In some examples, the computer-readable medium may store one or more executable instructions that, when executed, cause one or more processors to receive information from one or more sensors regarding weight distribution of a user of a guidance system, calculate a next movement for the user based on at least the information received from the one or more sensors, and transmit instructions to one or more actuators to effectuate at least one stimulus to direct the user's next movement.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

In the detailed description that follows, embodiments are described as illustrations only since various changes and modifications will become apparent to those skilled in the art from the following detailed description. The use of the same reference numbers in different figures indicates similar or identical items.

DETAILED DESCRIPTION

Figure 1:
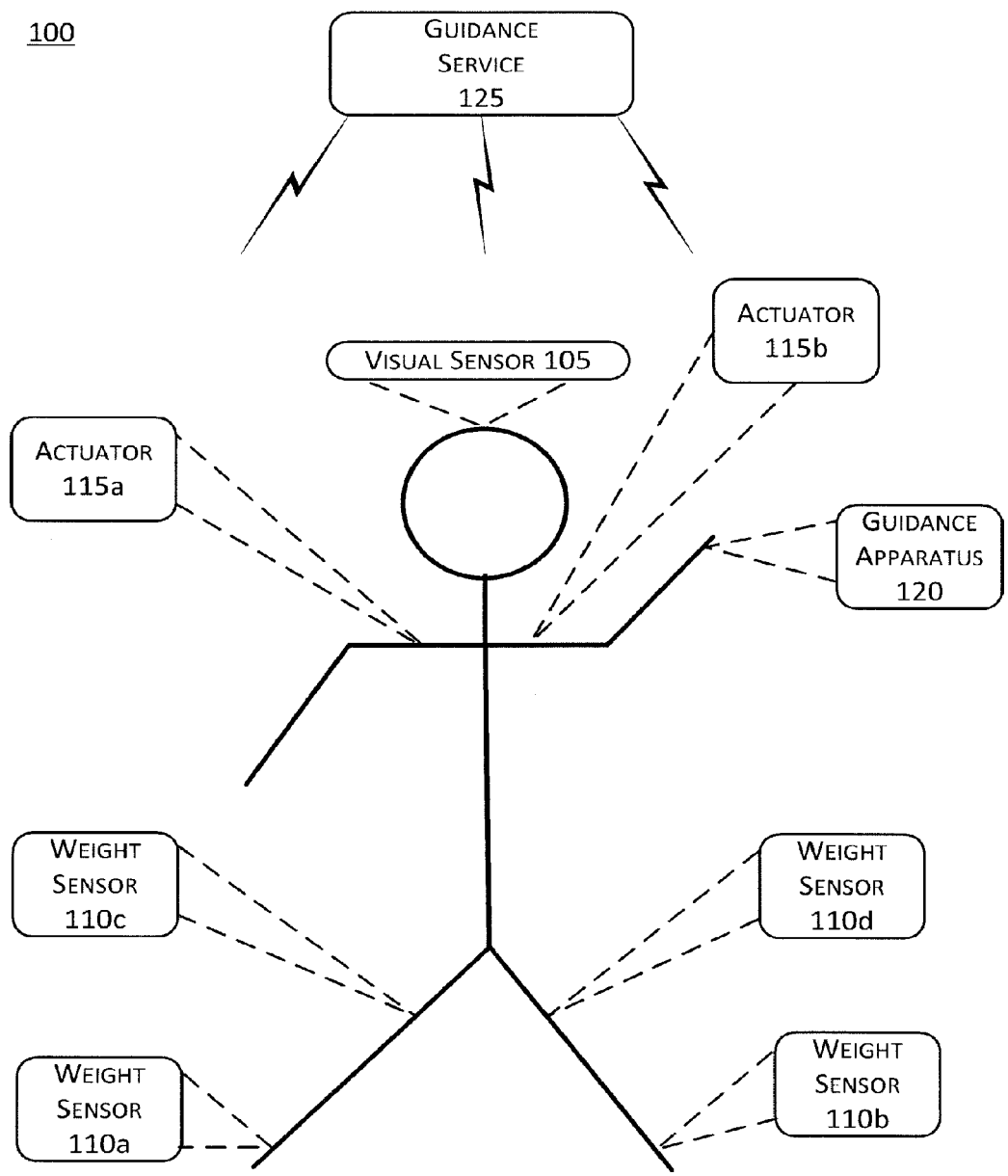
FIG. 1 shows an overview of an example guiding solution for a visually-impaired user in accordance with at least some embodiments described herein.

In the following detailed description, reference is made to the accompanying drawings, which form a part of the description. In the drawings, similar symbols typically identify similar components, unless context dictates otherwise. Furthermore, unless otherwise noted, the description of each successive drawing may reference features from one or more of the previous drawings to provide clearer context and a more substantive explanation of the current example embodiment. Still, the example embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

FIG. 1 shows an overview of an example guiding solution 100 for a visually-impaired user in accordance with at least some embodiments described herein.

Guiding solution 100 for guiding a visually-impaired user 102 includes at least a series of sensors including, e.g., a visual sensor 105 and weight sensors 110a-110d. It should be noted that the following description of, and references to, visual sensor 105 and weight sensors 110a-110d is by way of example only, as they may vary in quantity, placement, or even manner of placement on user 102. Further, throughout the following description, weight sensors 110a-110d may be collectively referred to as "weight sensors 110," particularly when describing the utility of the weight sensors themselves and, therefore, reference to the quantity thereof is not paramount.

Visual sensor 105 may be utilized to gather visual data regarding the physical surroundings of user 102, providing, in essence, a "birds-eye" view from the perspective of user 102. More specifically, visual sensor 105 may include a video camera, e.g., web-cam, and feedback mechanism to provide visual data regarding the physical surroundings of user 102, which may be factored into the calculation of instructions for a next movement therefore. Movements of user 102 include, by way of example and not limitation, a walking stride, a running stride, a stride up or down, e.g., a curb or a step, a hop or jump, or the like, or even any combination thereof.

Alternatively, visual sensor 105 may incorporate, or altogether be replaced by, a sonar-detecting device that may be utilized to provide sonar-based data regarding the physical surrounding of user 102, which may also be factored into the calculations of the instructions for a next movement of user 102.

Weight sensors 110 may be utilized to measure the current weight disposition of user 102. More specifically, weight sensors 110 may each be embedded with at least an angle detector and a feedback mechanism to provide data regarding the weight disposition of user 102, which may be used to determine an appropriate next movement for user 102.

For example, if user 102 is intended to turn 90 degrees to the right, the next stride may include user 102 using her right foot as a pivot to move her left foot 90 degrees to the right; or, alternatively, the next stride may include user 102 planting her left foot and shuffling her right foot laterally to the right. The determination of which of the above example scenarios for user 102 making a 90 degree turn to the right is dependent upon how much of user 102's weight is detected by each of, e.g., weight sensors 110 a and 110 b and, in accordance with some embodiments, at which angle thereof. Further, the measurement of user 102's weight by each of, e.g., weight sensor 110 a and weight sensor 110 b, may be relative to each other, relative to a predetermined threshold value, etc.

As depicted in FIG. 1, weight sensors 110a and 110b may be configured to be disposed on the respective feet of user 102. As examples, weight sensors 110a and 110b may be respectively embedded in or on an ankle strap or foot sleeve that is worn on each leg of user 102, or weight sensors 110a and 110b may be respectively embedded in the shoes worn on each foot of user 102. An example of such weight sensors is implemented by Airun® in its Airun® Plus training shoes that have a sensor embedded in a sole of one shoe that recognizes movements made when the user thereof is walking or running. The sensor can measure the speed at which you are moving and the weight which is being put on the shoe with each stride.

Alternatively, FIG. 1 also depicts that weight sensors 110c and 110d may be configured to be disposed elsewhere on the lower torso of user 102 to illustrate other example placements thereof, e.g., on leg straps or sleeves having the aforementioned angle detector and feedback mechanism embedded therein.

Guiding solution 100 for guiding visually-impaired user 102 further includes at least a series of actuators including, e.g., actuators 115a and 115b. The following description of, and references to, actuators 115a and 115b is by way of example only. The actuators may vary in quantity, placement, or even manner of placement on user 102. Further, throughout the following description, actuators 115a and 115b may be collectively referred to as "actuators 115," particularly when describing the utility of the actuators themselves and, therefore, reference to the quantity thereof is not paramount.

Actuators 115 may be utilized to lead user 102 based on guidance instructions that have factored therein data from, at least, weight sensors 110 corresponding to the current weight distribution of user 102. More specifically, actuators 115 may each be embedded with at least a haptic device to provide timely guidance instructions for an appropriate next movement for user 102. For example, actuators 115 may provide user 102 with one or more haptic signals in the form of, e.g., pulses that may differ in length, quantity, intensity, and/or even placement, that may be interpreted by user 102 as a guidance instruction for a corresponding next movement. Thus, differences among the aforementioned pulses may be attributed to specific guidance instructions for different lengths and angles of horizontal and vertical movements or combinations thereof.

Non-limiting examples of actuators 115 may include haptic directional indicators that are configured to provide tactile stimuli that may be localized on a device and further customized in accordance with any of placement, intensity, duration, quantity, or any combination thereof.

As depicted in FIG. 1, actuators 115a and 115b may be configured to be disposed on the respective shoulders of user 102. As examples, actuators 115a and 115b may be respectively embedded in or on a strap or harness that is worn on each shoulder of user 102. Such a strap or harness may be implemented separately to be worn across each shoulder or collectively to be worn across both shoulders.

Alternatively, actuators 115a and 115b may be configured to be disposed elsewhere on user 102. For example, though not depicted in FIG. 1, actuators 115 may be respectively embedded in or on an ankle strap or sleeve that is worn on each leg of user 102, which may or may not also incorporate weight sensors 110. As a further example, actuators 115a and 115b may be disposed anywhere on the upper or lower torso of user 102, or embedded in or attached to straps or sleeves that fit onto a limb or extremity of user 102.

Guiding solution 100 for guiding visually-impaired user 102 may further include a guidance apparatus 120 in one or more embodiments thereof.

Guidance apparatus 120 may be a processor-implemented device that is utilized to receive information from at least one of visual sensor 105 and weight sensors 110, including information regarding the physical environment and current weight distribution of user 102; calculate an appropriate next movement for user 102 based on the information received from weight sensors 110 and, in one or more embodiments, the information received from visual sensor 105; and transmit instructions to at least one of actuators 115 to effectuate one or more signal, i.e., physical stimuli, to direct the next appropriate movement for user 102. Guidance apparatus 120 may be implemented as a single-use device or incorporated into a multi-purpose device, e.g., smart-phone. Regardless of its physical implementation, guidance apparatus 120 may incorporate therein a client application or program having executable instructions.

Guiding solution 100 for guiding visually-impaired user 102 may further include a guidance service 125 for one or more embodiments thereof.

Guidance service 125 may be a remote system that provides guidance for visually-impaired user 102. Guidance service 125 may be implemented as a web-based service to which user 102 registers prior to use. Using guidance service 125, a service operator (not shown) may receive information from at least one of visual sensor 105 and weight sensors 110, including information regarding the physical environment and current weight distribution of user 102; utilize an application or program to calculate a next appropriate movement for user 102 based on the information received from weight sensors 110 and, in one or more embodiments, from visual sensor 105; and transmit guidance instructions to at least one of actuators 115 to effectuate one or more signals, i.e., physical stimuli, to direct the next appropriate movement for user 102.

Guidance apparatus 120 and guidance service 125 may be considered to be superfluous; and therefore, it is unlikely that guidance apparatus 120 and guidance service 125 are included in a common usage scenario for guiding solution 100. However, at least one embodiment of guiding solution 100 may have user 102 using guidance service 125 in, e.g., an urban setting where wireless access thereto is efficiently maintained and cost-effective, and using guidance apparatus 120 in, e.g., a rural setting for which the aforementioned factors weigh in favor of a guiding solution that relies upon short-range communication technologies. Therefore, guidance apparatus 120 and guidance service 125 may be communicatively connected so as to exchange usage data for user 102.

Further, in alternative embodiments, either of guidance apparatus 120 or guidance service 125 may be communicatively connected to a gaming system that may receive information from at least one of visual sensor 105 and weight sensors 110; calculate an appropriate next movement for user 102 based on the information received from at least weight sensors 110; transmit instructions to at least one of actuators 115 to effectuate one or more signal to direct the next appropriate movement for user 102; and receive feedback on the movements of user 102 relative to the transmitted instructions. Such embodiments may be implemented as part of a gaming system or even training system that is hosted locally on a set-top box or virtually by a cloud computing system, and in which user 102 traverses a virtual environment for either entertainment or training purposes.

Figure 2:
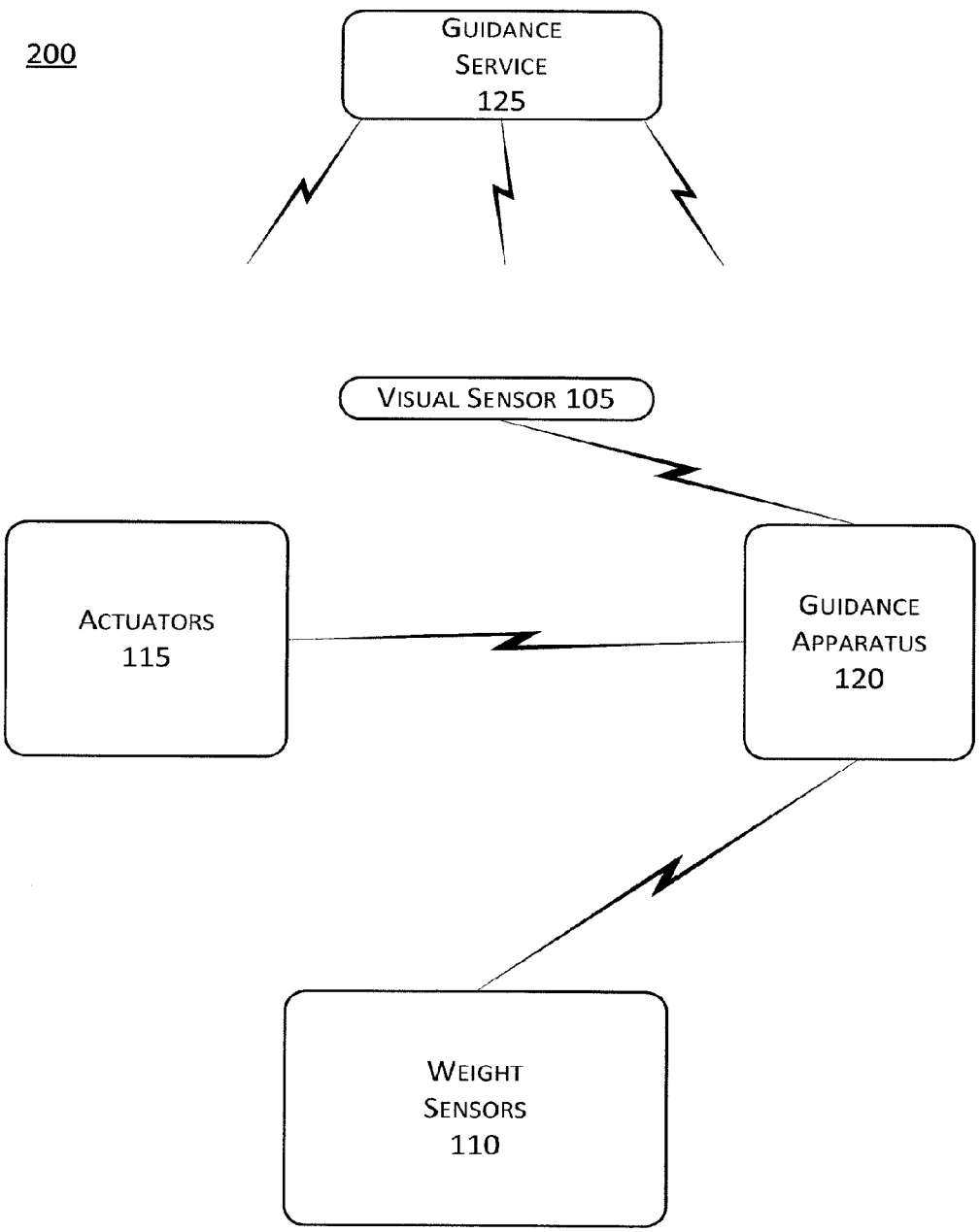
FIG. 2 shows an example communication model for an example guiding solution in accordance with at least some embodiments described herein.

FIG. 2 shows an example communication model 200 for an example guiding solution in accordance with at least some embodiments described herein.

As set forth above regarding guiding solution 100 in FIG. 1, guidance service 125 may be a remote system that provides guidance for visually-impaired user 102. Guidance service 125 may be implemented as a web-based service that is communicatively connected to at least one of visual sensor 105 and weight sensors 110 to receive data pertaining to user 102, as well as to at least one of actuators 115 to effectuate one or more signals or stimuli to direct a next appropriate movement for user 102. Thus, in accordance with at least one embodiment of communication model 200, corresponding to guiding solution 100, guidance service 125 may be communicatively connected to each of visual sensor 105, weight sensors 110, actuators 115, and even guidance apparatus 120 via, e.g., a wireless local area network technology (WLAN), Wi-Fi.

Visual sensor 105, in addition to being communicatively connected to guidance service 125 via, e.g., WLAN, may be implemented with a short-range communications transceiver such as, e.g., Bluetooth or Radio Frequency (RF), to serve as a feedback mechanism. Thus, visual sensor 105 may transmit visual data regarding the physical surroundings of user 102 to guidance service 125 via the corresponding WLAN feedback mechanism and/or to guidance apparatus 120 via the corresponding short-range communications transceiver.

Weight sensors 110, in addition to being communicatively connected to guidance service 125 via, e.g., WLAN, may also be implemented respectively with a short-range communications transceiver such as, e.g., Bluetooth or RF, to serve as a feedback mechanism. Thus, weight sensors 110 may transmit data regarding the current weight disposition of user 102 to guidance service 125 via the corresponding WLAN feedback mechanism and/or to guidance apparatus 120 via the corresponding short-range communications transceiver.

Actuators 115 also may be communicatively connected to guidance service 125 via, e.g., WLAN and, alternatively, be implemented with the short-range communications transceiver such as, e.g., Bluetooth or RF. Thus, actuators 115 may receive guidance instructions to direct a next appropriate movement for user 102 from guidance service 125 via the corresponding WLAN feedback mechanism or, in the alternative, from guidance apparatus 120 via the corresponding short-range communications transceiver.

Guidance apparatus 120, therefore, may be communicatively connected to any of visual sensor 105, weight sensors 110, and actuators 115 via the aforementioned short-range communications technology, with each having a corresponding short-range communications transceiver. Further still, although it is likely that guidance apparatus 120 and guidance service 125 may be superfluous within a common embodiment of guiding solution 100, there still may be scenarios in which both are utilized. Therefore, guidance apparatus 120 may also be provided with a WLAN transceiver to be communicatively connected with guidance service 125.

Figure 3:
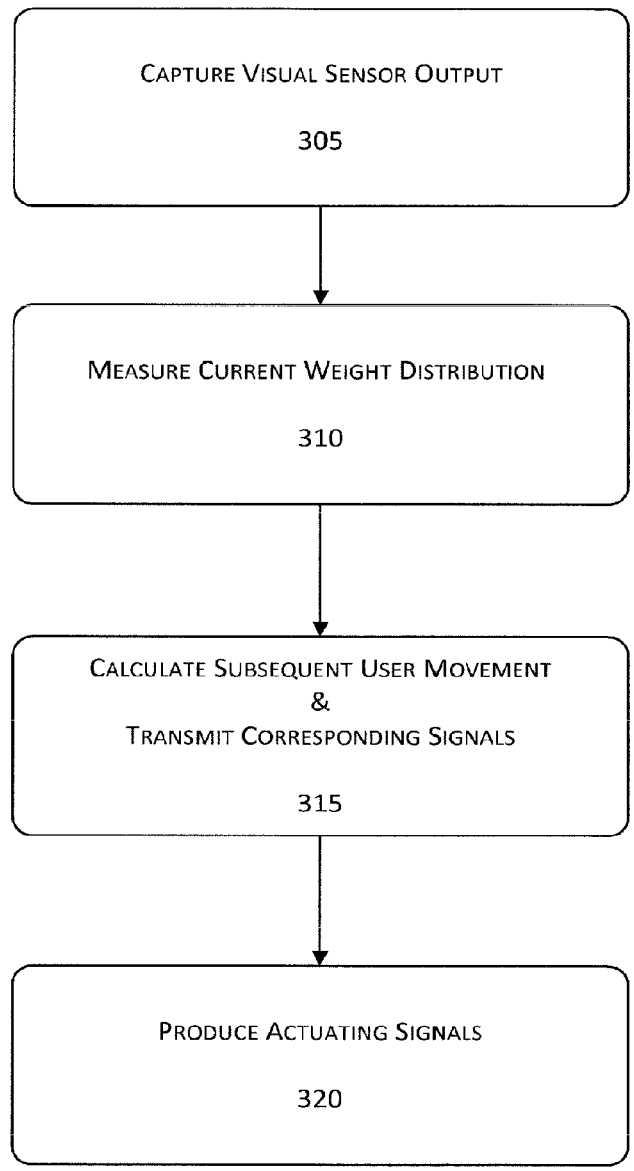
FIG. 3 shows a processing flow for an example guiding solution in accordance with at least some embodiments described herein.

FIG. 3 shows a processing flow 300 for an example guiding solution in accordance with at least some embodiments described herein. Processing flow 300 may include various operations, functions, or actions as illustrated by one or more of blocks 305, 310, 315, and/or 320.

More particularly, processing flow 300 describes sub-processes executed by various components that are part of guiding solution 100. However, processing flow 300 is not limited to such components, as obvious modifications may be made by re-ordering two or more of the sub-processes described here, eliminating at least one of the sub-processes, adding further sub-processes, substituting components, or even having various components assuming sub-processing roles accorded to other components in the following description.

Block 305 (Capture Visual Sensor Output) may represent visual sensor 105 capturing visual data regarding the physical surroundings of user 102.

As set forth above, visual sensor 105 may include a video camera, e.g., web-cam to capture visual data regarding the physical surroundings of user 102, which may be factored into the calculation of instructions for a next appropriate movement for user 102. In FIG. 1, visual sensor 105 is depicted as being coupled to the head of user 102, e.g., strapped to a headband. However, other implementations may certainly be considered, such as visual sensor 105 being affixed to a safety vest worn by user 102, visual sensor 105 being a smart-phone video camera, visual sensor 105 being incorporated into guidance apparatus 120, or any combination thereof. That is, visual sensor 105 may adorn user 102 in any manner that provides a clear view, i.e., "birds-eye view," of the physical surroundings, including any static or dynamic obstacles proximate to user 102.

Alternatively, block 305 may represent the capturing of data based on sonar readings captured by a sonar-detecting device that has replaced, or is in combination with, visual sensor 105. In this alternative embodiment, the captured data may be processed into data that provides an accurate depiction of the physical surroundings of user 102, with such processing occurring locally at sensor 105 or remotely by a program or application at guidance apparatus 120 or guidance service 125.

Regardless, the captured visual data regarding the physical surroundings of user 102 may be transmitted from visual sensor 105 via a feedback mechanism in the form of, e.g., a WLAN transceiver or a short-range communication transceiver.

In yet another alternative embodiment, block 305 may represent the capturing of visual data from external sources such as, but not limited to, municipal cameras or even a GPS (global positioning system) satellite that are able to capture an extended view of the geographic movements of user 102 with a high level of detail regarding the physical surroundings of user 102. According to such embodiments of flow 300 for guiding solution 100, the captured visual data regarding the movements and physical surroundings of user 102 may be transmitted from the source thereof in the form of, e.g., a WLAN connection or even a LAN connection. Block 305 may be followed by block 310.

Block 310 (Measure Current Weight Distribution) may represent weight sensors 110 measuring current weight disposition, with angular measurements thereof, of user 102.

As set forth above, weight sensors 110 may include at least an angle detector and a feedback mechanism to provide data regarding the weight disposition of user 102. Whether weight sensors 110a and 110b are disposed on the respective feet of user 102 in the form of an ankle strap or foot sleeve that is worn on each leg of user 102 or whether weight sensors 110a and 110b are embedded in the shoes worn on each foot of user 102, or a combination thereof, weight sensors 110 may include both a right leg and a left leg component. Further, to accurately measure a current weight disposition of user 102, weight sensors 110 may further include, for both of the right leg and left leg component, one or more right and left portion sub-components to even more precisely measure a current weight disposition of each leg and foot of user 102.

Regardless, the measured data regarding the current weight disposition of user 102 may be transmitted from weight sensors 110 via a feedback mechanism in the form of, e.g., a WLAN transceiver or a short-range communication transceiver. Block 310 may be followed by block 315.

Block 315 (Calculate Subsequent User Movement & Transmit Corresponding Signals) may represent either of guidance apparatus 120 and guidance service 125 receiving the captured visual sensor data and the measured current weight disposition data of user 102 to calculate, and to subsequently transmit corresponding data for, an appropriate next movement for user 102.

As set forth above, guidance apparatus 120 may be communicatively connected to any of visual sensor 105 and weight sensors 110 via short-range communications technology, with each sensor having a corresponding short-range communications transceiver.

Further still, web-based guidance service 125 may be may be communicatively connected to any of visual sensor 105 and weight sensors 110 via, e.g., WLAN technology, with each having an appropriate transceiver incorporated therein.

Regardless, both of guidance apparatus 120 and guidance service 125 may include an application or program to receive at least one of: the visual sensor output from visual sensor 105, an alternative sonar-detecting device, a series of municipal cameras, a GPS satellite, or a combination thereof, regarding the geographic movement and physical environment of user 102; and the measured data from weight sensors 110 regarding the current weight distribution of user 102.

The aforementioned application or program may then execute processing to calculate an appropriate next movement for user 102 by utilizing an algorithm that takes into account at least one of the received visual sensor output that is indicative of a current geographic location of user 102, including any static and dynamic obstacles in the path of user 102, and the received measured data regarding the current weight distribution of user 102. Accordingly, the application or program may determine how to appropriately guide user 102.

To appropriate guide user 102, calculated guidance instructions may include a directional component as well as a timing component. Even more particularly, the directional component of the guidance instructions may include at least one of a horizontal sub-component and a vertical sub-component, with both having an angular sub-component. Therefore, the application or program corresponding to either of guidance apparatus 120 and guidance service 125, or even an operator for guidance service 125, may calculate real-time guidance instructions that enable visually-impaired user 102 to move rapidly through a geographic territory of expanding scope confident of avoiding static and dynamic obstacles that may otherwise impede such movement.

Having calculated the guidance instructions, the aforementioned application or program for either of guidance apparatus 120 and guidance service 125 may then transmit the guidance instructions to at least one of actuators 115 corresponding to user 102 to effectuate one or more signals, i.e., physical stimuli, to direct the next movement for user 102. Block 315 may be followed by block 320.

Block 320 (Produce Actuating Signals) may represent actuators 115, which may be communicatively connected to guidance apparatus 120 via a short-range communications technology and/or to guidance service 125 via, i.e., WLAN, receiving one or more guidance instructions to produce actuating signals to direct an appropriate next movement for user 102.

As set forth above, actuators 115a and 115b may, as examples only, be respectively embedded in or on a strap or harness that is worn on each shoulder of user 102 either separately on each shoulder or collectively across both shoulders. Alternatively, actuators 115a and 115b may be disposed elsewhere on user 102, such as in or on an ankle strap or sleeve that is worn on each leg of user 102, which may or may not also incorporate sensors 110.

Regardless, actuators 115 may receive the calculated guidance instructions from either guidance apparatus 120 or guidance service 125, and translate the received signals into physical stimuli that may be interpreted by user 102 as instructions for a subsequent physical movement. Again, the guidance instructions may include a directional component as well as a timing component. Even more particularly, the directional component of the guidance instructions may include a horizontal sub-component, a vertical sub-component, with both having an angular sub-component.

Accordingly, the physical stimuli produced by actuators 115 may include a series of pulses that may vary in terms of intensity, duration, quantity, placement, or any combination thereof, with the aforementioned variations in stimuli respectively corresponding to variations in horizontal and/or vertical stride direction, stride length, stride angle, stride depth, stride height, or even stride rate for user 102. Of course, effective implementation of guiding solution 100 may entail training for user 102 to properly and briskly interpret the stimuli provided by actuators 115.

Figure 4:
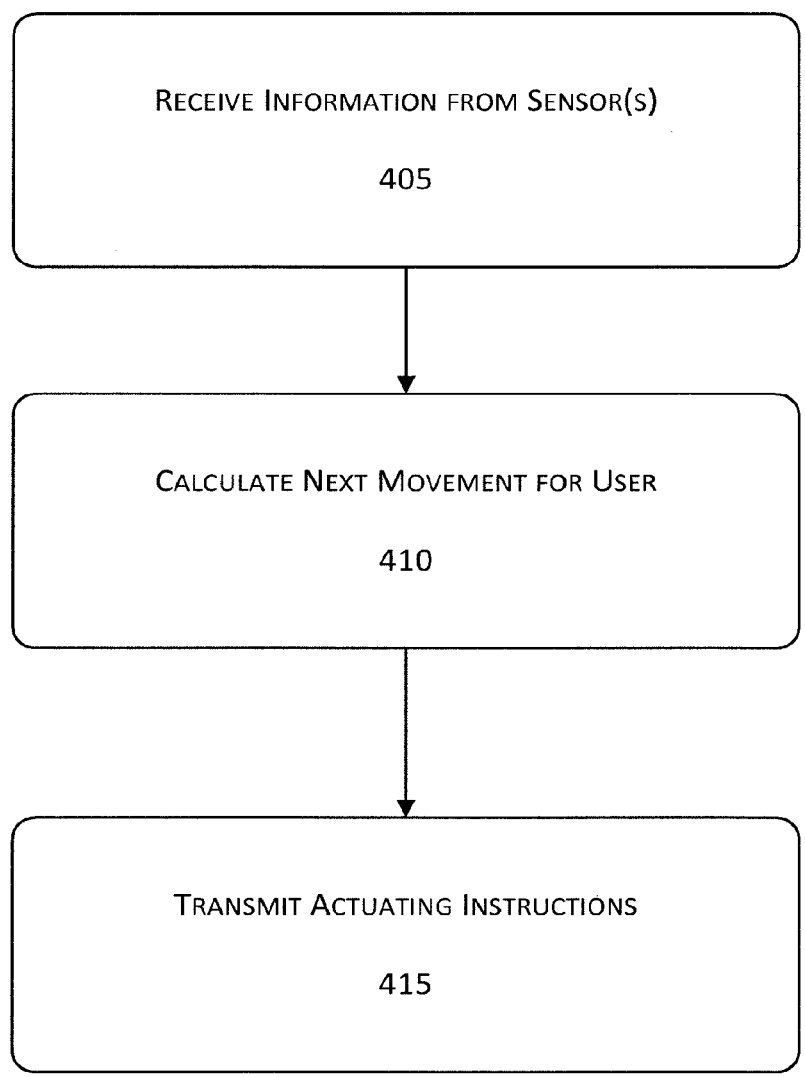
FIG. 4 shows a processing flow for an example guidance apparatus in accordance with at least some embodiments described herein.

FIG. 4 shows a processing flow 400 for an example guidance apparatus in accordance with at least some embodiments described herein. Processing flow 400 may include various operations, functions, or actions as illustrated by one or more of blocks 405, 410, and/or 415.

More particularly, processing flow 400 describes sub-processes executed at or by guidance apparatus 120 or guidance service 125. However, processing flow 400 is not so limited, as obvious modifications may be made by re-ordering two or more of the sub-processes described here, eliminating at least one of the sub-processes, adding further sub-processes, or even having guidance apparatus 120 and guidance service 125 execute sub-processing in tandem.

Block 405 (Receive Information from Sensors(s)) may represent either of guidance apparatus 120 and guidance service 125 receiving information from various sensors, including visual sensor 105 and weight sensors 110 either singularly or in combination.

As set forth above, guidance apparatus 120 may be communicatively connected to any of visual sensor 105 and weight sensors 110 via short-range communications technology, with each having a corresponding short-range communications transceiver; and web-based guidance service 125 may be may be communicatively connected to any of visual sensor 105 and weight sensors 110 via, e.g., WLAN, with each having an appropriate transceiver incorporated therein.

Further, both of guidance apparatus 120 and guidance service 125 may include an application or program to receive at least one of sensor output from visual sensor 105, an alternative sonar-detecting device, municipal cameras, a GPS satellite, or a combination thereof, regarding the geographic movement and physical environment of user 102; and the measured data from weight sensors 110 regarding the current weight distribution of user 102. Block 405 may be followed by block 410.

Block 410 (Calculate Next Movement for User) may represent the application or program included within either of guidance apparatus 120 and guidance service 125 calculating an appropriate next movement for user 102 by taking into account at least one of the received visual sensor output that is indicative of a current geographic location and physical environment of user 102 and the received measured data regarding the current weight distribution of user 102. Accordingly, the application or program may determine how to appropriately guide user 102. Block 410 may be followed by block 415.

Block 415 (Transmit Actuating Instructions) may represent the aforementioned application or program for either of guidance apparatus 120 and guidance service 125 transmitting the guidance instructions to at least one of actuators 115 corresponding to user 102 to effectuate one or more signals, i.e., physical stimuli, to direct the appropriate next movement for user 102.

The transmitting effected at block 415 may be via short-range communications technology from guidance apparatus 120 or via WLAN technology from guidance service 125.

Consequently, either of guidance apparatus 120 and guidance service 125 may transmit to actuators 115 the calculated guidance instructions. The guidance instructions may be translated for actuation at either of guidance apparatus 120 and guidance service 125 before the aforementioned transmission; or the guidance instructions may be translated for actuation as physical stimuli at the appropriate ones of actuators 115 upon receipt thereof. Again, the guidance instructions may include a directional component as well as a timing component. Even more particularly, the directional component of the guidance instructions may include a horizontal sub-component, a vertical sub-component, with both having an angular sub-component.

In accordance with the above description, a guiding solution for visually-impaired users may be implemented utilizing measured data regarding the weight disposition, including angular components thereof, of the user.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent processes and even apparatuses within the scope of the disclosure, in addition to those described herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that the terminology used herein is for the purpose of describing particular embodiments only, and is not intended to be limiting.

Figure 5:
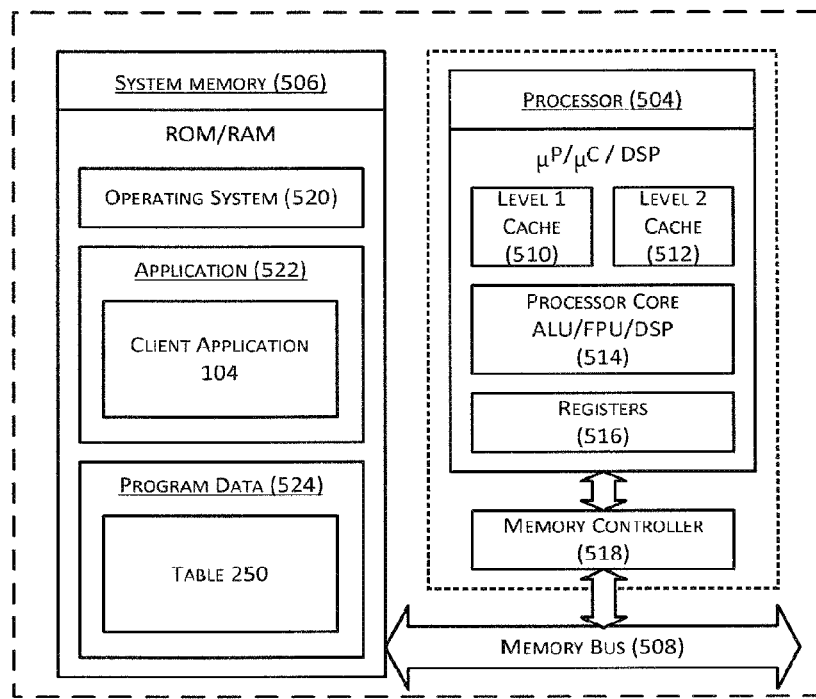
FIG. 5 shows a block diagram illustrating an example computing device by which various embodiments of the example solutions described herein may be implemented.

FIG. 5 shows a block diagram illustrating an example computing device 500 by which various embodiments of the example solutions described herein may be implemented.

More particularly, FIG. 5 shows an illustrative computing embodiment, in which any of the processes and sub-processes described herein may be implemented as computer-readable instructions stored on a computer-readable medium. The computer-readable instructions may, for example, be executed by a processor of a mobile unit, a network element, and/or any other computing device, particularly as applicable to the applications and/or programs described above corresponding to guidance apparatus 120 and guidance service 125.

In a very basic configuration 502, a computing device 500 may typically include one or more processors 504 and a system memory 506. A memory bus 508 may be used for communicating between processor 504 and system memory 506.

Depending on the desired configuration, processor 504 may be of any type including but not limited to a microprocessor (µP), a microcontroller (µC), a digital signal processor (DSP), or any combination thereof. Processor 504 may include one or more levels of caching, such as a level one cache 510 and a level two cache 512, a processor core 514, and registers 516. An example processor core 514 may include an arithmetic logic unit (ALU), a floating point unit (FPU), a digital signal processing core (DSP Core), or any combination thereof. An example memory controller 518 may also be used with processor 504, or in some implementations memory controller 518 may be an internal part of processor 504.

Depending on the desired configuration, system memory 506 may be of any type including but not limited to volatile memory (such as RAM), non-volatile memory (such as ROM, flash memory, etc.) or any combination thereof. System memory 506 may include an operating system 520, one or more applications 522, and program data 524.

Application 522 may include the aforementioned applications or programs that are arranged to perform the functions ascribed to either of guidance apparatus 120 and guidance service 125, which are described previously with respect to FIGS. 1-4. Program data 524 may include a table 250, which may be useful for implementing device discovery as described herein.

System memory 506 is an example of computer storage media. Computer storage media may include, but not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 500. Any such computer storage media may be part of computing device 500.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 500 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 500 may also be implemented as a personal computer including both laptop computer and non-laptop computer configurations.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein may be implemented, e.g., hardware, software, and/or firmware, and that the preferred vehicle may vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes for guiding solution 100 via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers, e.g., as one or more programs running on one or more computer systems, as one or more programs running on one or more processors, e.g., as one or more programs running on one or more microprocessors, as firmware, or as virtually any combination thereof, and that designing the circuitry and/or writing the code for the software and/or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors, e.g., feedback for sensing position and/or velocity; control motors for moving and/or adjusting components and/or quantities. A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

Lastly, with respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims, e.g., bodies of the appended claims, are generally intended as "open" terms, e.g., the term "including" should be interpreted as "including but not limited to," the term "having" should be interpreted as "having at least," the term "includes" should be interpreted as "includes but is not limited to," etc. It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an," e.g., "a" and/or "an" should be interpreted to mean "at least one" or "one or more;" the same holds true for the use of definite articles used to introduce claim recitations. In addition, even if a specific number of an introduced claim recitation is explicitly recited, those skilled in the art will recognize that such recitation should be interpreted to mean at least the recited number, e.g., the bare recitation of "two recitations," without other modifiers, means at least two recitations, or two or more recitations. Furthermore, in those instances where a convention analogous to "at least one of A, B, and C, etc." is used, in general such a construction is intended in the sense one having skill in the art would understand the convention, e.g., "a system having at least one of A, B, and C" would include but not be limited to systems that have A alone, B alone, C alone, A and B together, A and C together, B and C together, and/or A, B, and C together, etc. In those instances where a convention analogous to "at least one of A, B, or C, etc." is used, in general such a construction is intended in the sense one having skill in the art would understand the convention, e.g., "a system having at least one of A, B, or C" would include but not be limited to systems that have A alone, B alone, C alone, A and B together, A and C together, B and C together, and/or A, B, and C together, etc. It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

The invention claimed is:

1. A user-guidance system, comprising:
   sensors to measure current weight distribution on one of a user's legs;
   a visual sensor to gather visual information regarding the user's current geographic location and physical surroundings including any obstacles;
   a guidance apparatus to:
      receive the measured current weight distribution from the sensors,
      receive the gathered visual information regarding the user's current geographic location and physical surroundings including any obstacles from the visual sensor, and
      calculate a subsequent stride for one of the user's legs based on at least the received weight distribution data of the one of the user's legs and the received visual information, wherein the calculated subsequent stride for one of the user's legs includes a horizontal stride direction, a vertical stride direction, a stride length, a stride angle, a stride depth, a stride height, and a stride rate for the subsequent stride for one of the user's legs; and
   an actuator to provide timely guidance instructions for an appropriate subsequent stride for the user by:
      producing actuating signals based on at least the calculated subsequent stride for one of the user's legs, and
      transmitting the actuating signals to instruct the subsequent stride for one of the user's legs.

2. The user-guidance system of claim 1, wherein the sensors are configured to be attached to at least one of the user's shoes.

3. The user-guidance system of claim 1, wherein the sensors are configured to be user-adorned and transmit the measured weight distribution data via a short-range communication system.

4. The user-guidance system of claim 1, wherein the guidance apparatus is configured to be embedded in a smart phone.

5. The user-guidance system of claim 1, wherein the guidance apparatus is configured to be user-retained and transmit the actuating signals to instruct the subsequent stride for one of the user's legs via a short-range communication system.

6. The user-guidance system of claim 1, wherein the actuator is configured to be worn across upper torso of the user.

7. The user-guidance system of claim 1, wherein the actuator is configured to be attached to the sensors.

8. The user-guidance system of claim 1, wherein the actuating signals differ in length, number, or intensity.

9. A guidance system, comprising:
   at least one weight sensor to determine current weight distribution on one of a user's legs;
   a visual sensor to provide visual data regarding the user's physical surroundings including any obstacles;
   a guiding device to:
      receive the determined current weight distribution from the at least one weight sensor, receive the visual data regarding the user's physical surroundings including any obstacles from the visual sensor, and translate a subsequent stride for one of the user's legs in response to the received current weight distribution on one of the user's legs and the received visual data into instructions to direct the user's physical stride for one of the user's legs, wherein the translated subsequent stride for one of the user's legs includes a horizontal stride direction, a vertical stride direction, a stride length, a stride angle, a stride depth, a stride height, and a stride rate for the subsequent stride for one of the user's legs; and at least one actuator, to provide timely guidance instructions for an appropriate subsequent stride for the user, configured to translate the instructions from the guiding device into at least one appropriate physical stimulus to direct the subsequent stride for one of the user's legs.

10. The guidance system of claim 9, wherein the at least one weight sensor is configured to be embedded within at least one shoe worn by the user.

11. The guidance system of claim 9, wherein the at least one weight sensor is configured to be worn on at least one foot by the user.

12. The guidance system of claim 9, wherein the at least one weight sensor determines the user's trajectory based on the current weight distribution.

13. The guidance system of claim 9, wherein the at least one weight sensor is configured to be included within a same device as the at least one actuator.

14. The guidance system of claim 9, wherein the at least one weight sensor is communicatively connected to the guiding device via a short-range communication system.

15. The guidance system of claim 9, wherein the at least one weight sensor is communicatively connected to the guiding device via a Bluetooth connection.

16. The guidance system of claim 9, wherein the at least one weight sensor is communicatively connected to the guiding device via a radio frequency connection.

17. The guidance system of claim 9, wherein the at least one weight sensor is communicatively connected to the guiding device via a wireless internet connection.

18. The guidance system of claim 9, wherein the visual sensor is a camera that is configured to be user-adorned and is communicatively connected to the guiding device via a short-range communication system.

19. The guidance system of claim 9, wherein the visual sensor is a camera that is configured to be user-adorned and is communicatively connected to the guiding device via a radio frequency connection.

20. The guidance system of claim 9, wherein the visual sensor is a camera that is configured to be user-adorned and is communicatively connected to the guiding device via a wireless internet connection.

21. The guidance system of claim 9, wherein the guiding device is configured to be disposed on the user.

22. The guidance system of claim 9, wherein the guiding device is embedded within a smart phone.

23. The guidance system of claim 9, wherein the guiding device is to provide the instructions as facilitated by a guiding device operator.

24. The guidance system of claim 9, wherein the at least one actuator is configured to be user-adorned and is communicatively connected to the guiding device via a short-range communication system.

25. The guidance system of claim 9, wherein the at least one actuator is configured to be user-adorned and is communicatively connected to the guiding device via a radio frequency connection.

26. The guidance system of claim 9, wherein the at least one appropriate physical stimulus to direct the user's strides includes a series of pulses that vary in at least one of intensity, duration, and quantity.

27. A non-transitory computer-readable medium that stores one or more executable instructions that, when executed, cause one or more processors to:

receive information from a visual sensor regarding physical surroundings of a user of a guidance system including any obstacles and one or more sensors regarding current weight distribution on one of the user's legs;

calculate a next stride for one of the user's legs based on at least the information regarding current weight distribution on one of the user's leg received from the one or more sensors and the information regarding physical surroundings of the user of the guidance system including any obstacles received from the visual sensor, wherein the calculated next stride for one of the user's legs includes a horizontal stride direction, a vertical stride direction, a stride length, a stride angle, a stride depth, a stride height, and a stride rate for the next stride for one of the user's legs; and transmit instructions to one or more actuators to provide timely guidance instructions for an appropriate next stride for the user, wherein the one or more actuators are configured to effectuate at least one stimulus to direct the next stride for one of the user's legs.

28. The non-transitory computer-readable medium of claim 27, wherein the instructions transmitted to the actuators effectuate at least one stimulus to direct a velocity of the next stride for one of the user's legs.

29. The non-transitory computer-readable medium of claim 27, wherein the non-transitory computer-readable medium is configured to be held by the user.

30. The non-transitory computer-readable medium of claim 27, wherein the non-transitory computer-readable medium is disposed at a location remote from the user.

31. The non-transitory computer-readable medium of claim 27, wherein the at least one stimulus is a series of pulses that vary in length, quantity, or intensity.

32. The non-transitory computer-readable medium of claim 27, wherein the at least one stimulus indicates a direction for the next stride.

33. The non-transitory computer-readable medium of claim 27, wherein the processors are included in a set-top box gaming console.

34. The non-transitory computer-readable medium of claim 27, wherein the processors are included in an on-line gaming system.

* * * * *